(12) United States Patent
Hanawa et al.

(10) Patent No.: US 11,375,696 B2
(45) Date of Patent: Jul. 5, 2022

(54) BELT COVER

(71) Applicants: ANICALL CORPORATION, Kanagawa (JP); TOYOBO STC CO., LTD., Osaka (JP); TOYOBO CO., LTD., Osaka (JP)

(72) Inventors: Akira Hanawa, Kanagawa (JP); Yuichiro Omote, Osaka (JP); Hideki Kawabata, Osaka (JP); Kazunori Hirata, Osaka (JP); Euichul Kwon, Shiga (JP)

(73) Assignees: ANICALL CORPORATION, Kanagawa (JP); TOYOBO STC CO., LTD., Osaka (JP); TOYOBO CO., LTD., Osaka (JP)

( * ) Notice: Subject to any disclaimer, the term of this patent is extended or adjusted under 35 U.S.C. 154(b) by 269 days.

(21) Appl. No.: 16/313,737

(22) PCT Filed: Jul. 19, 2017

(86) PCT No.: PCT/IB2017/000843
§ 371 (c)(1),
(2) Date: Dec. 27, 2018

(87) PCT Pub. No.: WO2018/002705
PCT Pub. Date: Jan. 4, 2018

(65) Prior Publication Data
US 2019/0313607 A1    Oct. 17, 2019

(30) Foreign Application Priority Data

Jun. 29, 2016  (JP) .............................. JP2016-129231
Jul. 19, 2016  (JP) .............................. JP2016-141730

(51) Int. Cl.
| | |
|---|---|
| *A61B 5/00* | (2006.01) |
| *A01K 29/00* | (2006.01) |
| *A61B 5/25* | (2021.01) |
| *A61B 5/349* | (2021.01) |
| *B68C 1/02* | (2006.01) |
| *A61B 5/291* | (2021.01) |

(52) U.S. Cl.
CPC .............. *A01K 29/005* (2013.01); *A61B 5/00* (2013.01); *A61B 5/25* (2021.01); *A61B 5/349* (2021.01);
(Continued)

(58) Field of Classification Search
CPC .... A01K 29/005; A61B 5/04; A61B 5/04087; A61B 5/683; A61B 5/6801; A61B 5/6831; A61D 17/00
See application file for complete search history.

(56) References Cited

U.S. PATENT DOCUMENTS

| | | |
|---|---|---|
| 4,478,225 A | 10/1984 | Ewing |
| 4,540,001 A | 9/1985 | Ewing |

(Continued)

FOREIGN PATENT DOCUMENTS

| | | |
|---|---|---|
| JP | 3164393 | 5/2001 |
| WO | 2004/084624 | 10/2004 |

OTHER PUBLICATIONS

Extended European Search Report dated May 4, 2020 in European Patent Application No. 17819425.4.
(Continued)

*Primary Examiner* — Benyam Haile
(74) *Attorney, Agent, or Firm* — Wenderoth, Lind & Ponack, L.L.P.

(57) ABSTRACT

A belt cover for attaching to a horse The belt cover including at least (1) an electrode for detecting a bioelectric signal by contacting with the surface of a body of the horse, (2) an electric wiring, and (3) a connector for connecting with the electric wiring through a part for connecting with the connector and the electric wiring. Each of the electrode and the electric wiring includes a stretchable conductor having a conductive particle including a silver particle and a binder resin. The stretchable conductor of the electrode and the (Continued)

electric wiring has a sheet resistance of 0.1Ω☐ or less, an insulating layer is laminated on the electric wiring, and the electrode and the electric wiring are integrally formed without joints.

12 Claims, 5 Drawing Sheets

(52) U.S. Cl.
CPC .............. *A61B 5/683* (2013.01); *A61B 5/291* (2021.01); *A61B 5/6802* (2013.01); *B68C 1/02* (2013.01)

(56) References Cited

U.S. PATENT DOCUMENTS

| | | | |
|---|---|---|---|
| 6,504,483 B1 | 1/2003 | Richards et al. | |
| 9,161,878 B1* | 10/2015 | Pamplin | A61H 7/001 |
| 9,414,758 B1* | 8/2016 | Brockway | A61B 5/726 |
| 2006/0122528 A1* | 6/2006 | Gal | A61B 5/6831 600/534 |
| 2006/0173367 A1* | 8/2006 | Stuart | A01K 15/02 600/508 |
| 2009/0229039 A1* | 9/2009 | Kuck | A41D 13/1254 2/338 |
| 2011/0237921 A1 | 9/2011 | Askin, III et al. | |

OTHER PUBLICATIONS

International Search Report dated Oct. 31, 2017 in International (PCT) Application No. PCT/IB2017/000843.

Taiwanese Office Action dated Dec. 11, 2020 in corresponding Taiwanese Application No. 106124200, with English Translation.

Australian Examination Report dated Dec. 14, 2021 in corresponding AU application No. 2017287880.

* cited by examiner

[FIG.1]
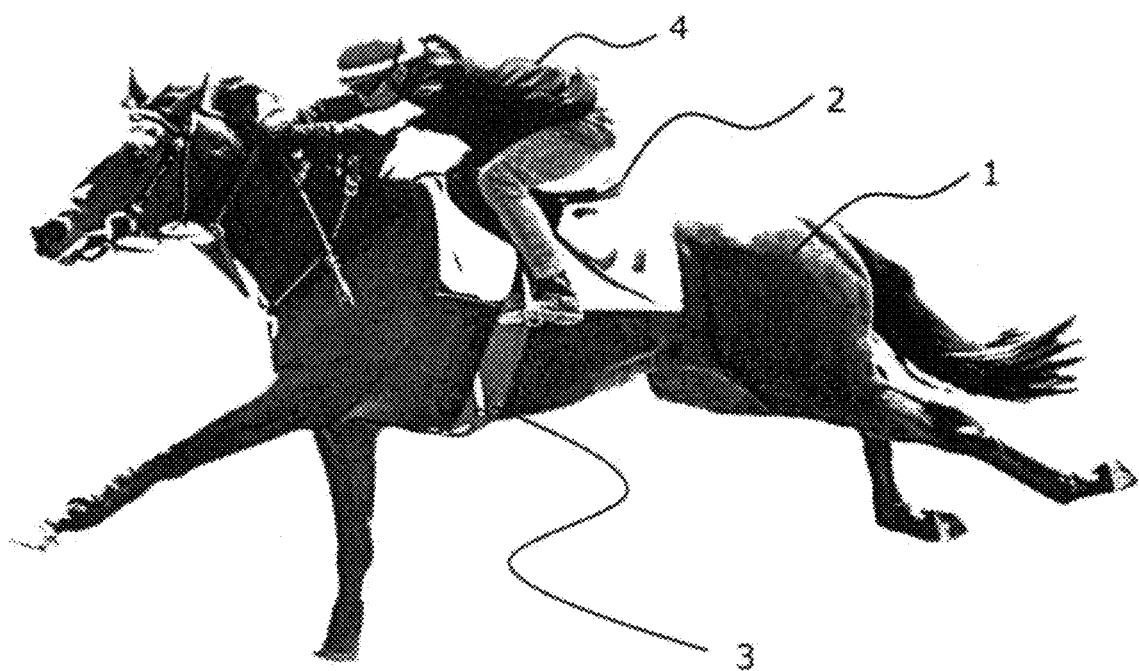

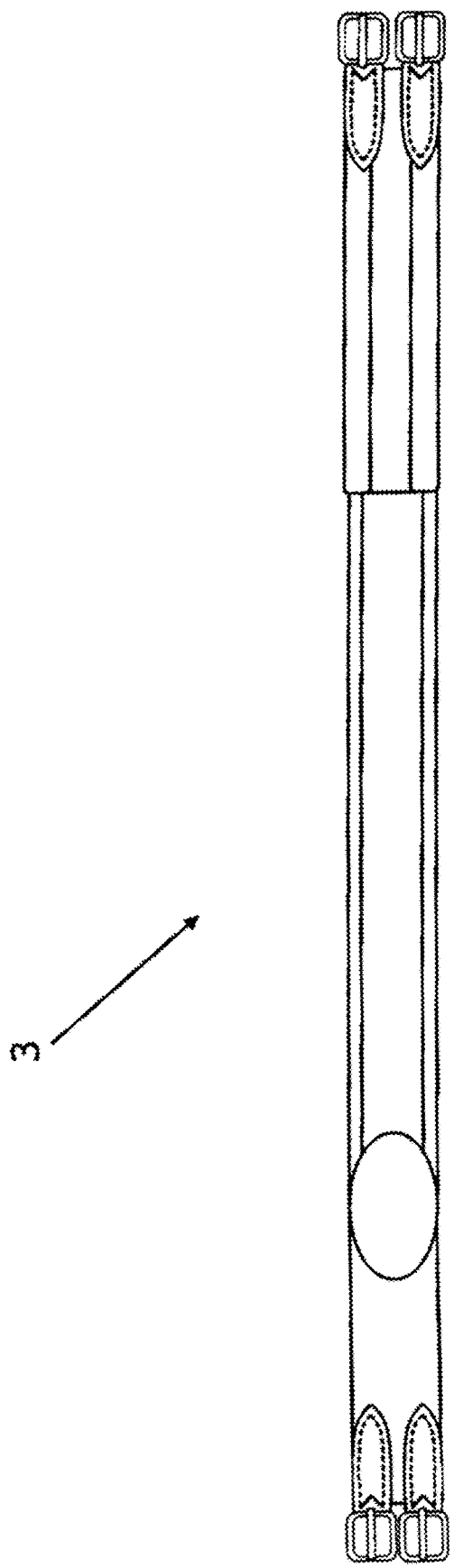
[FIG.2]

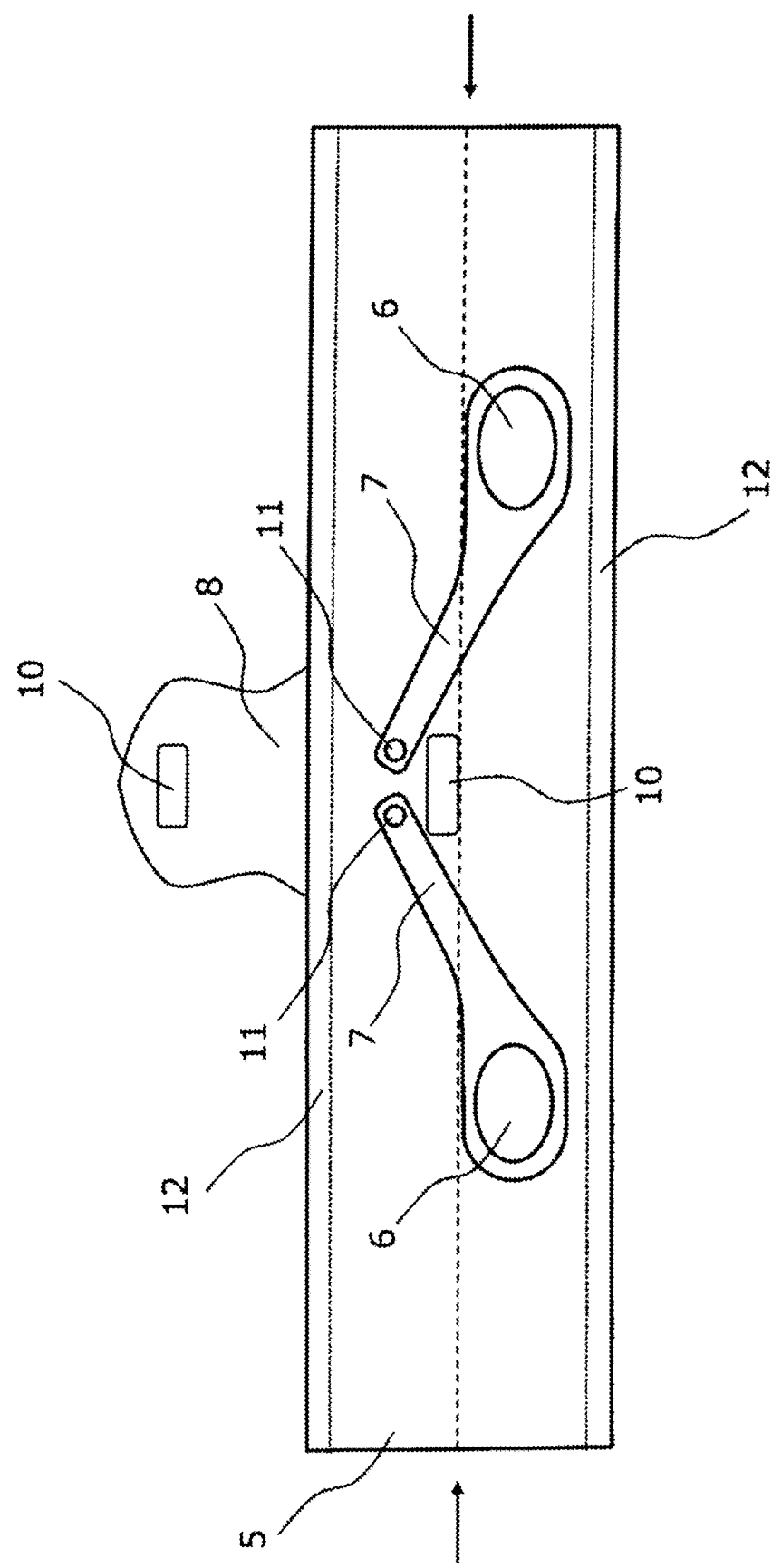
[FIG.3]

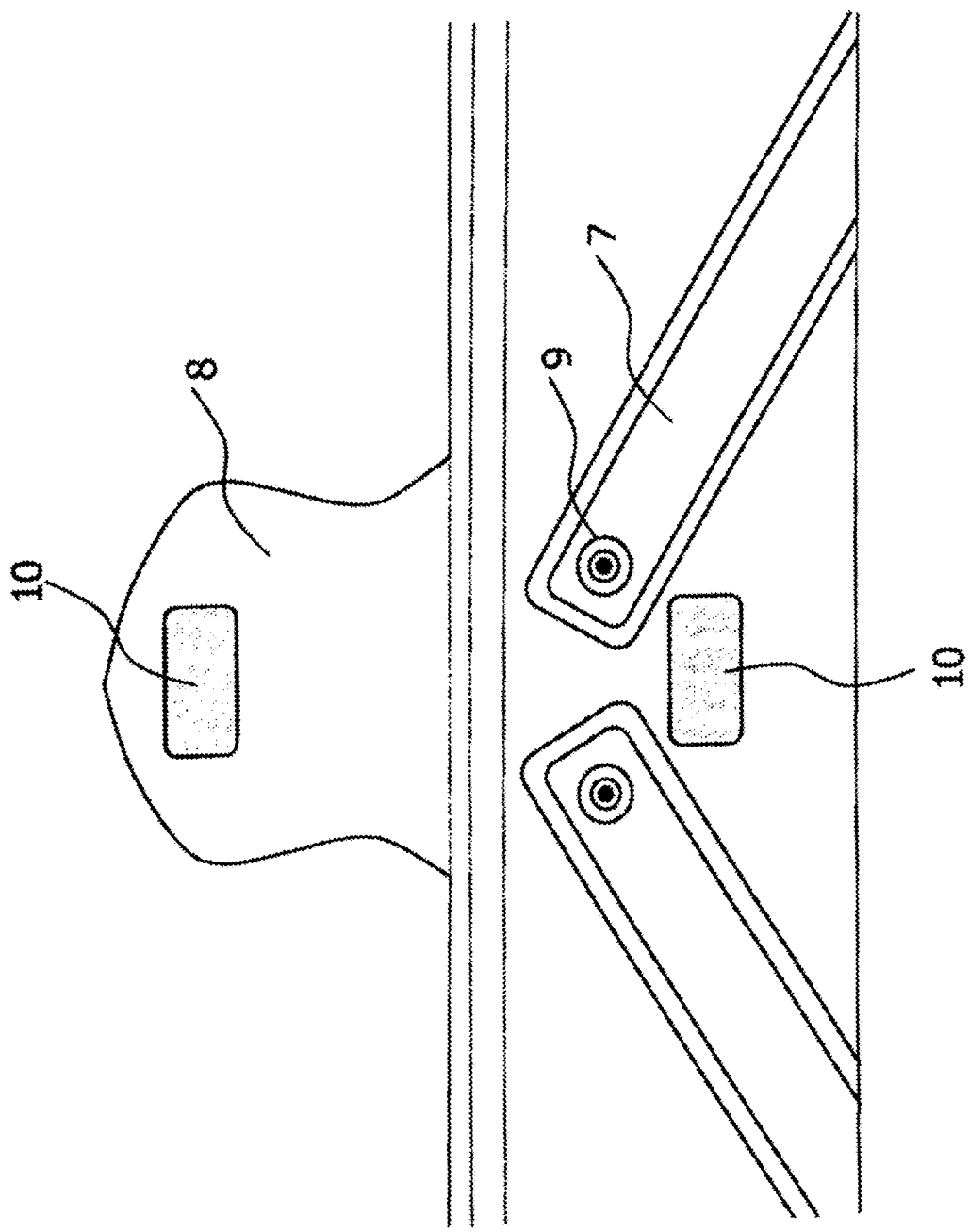
[FIG. 4]

[FIG.5]
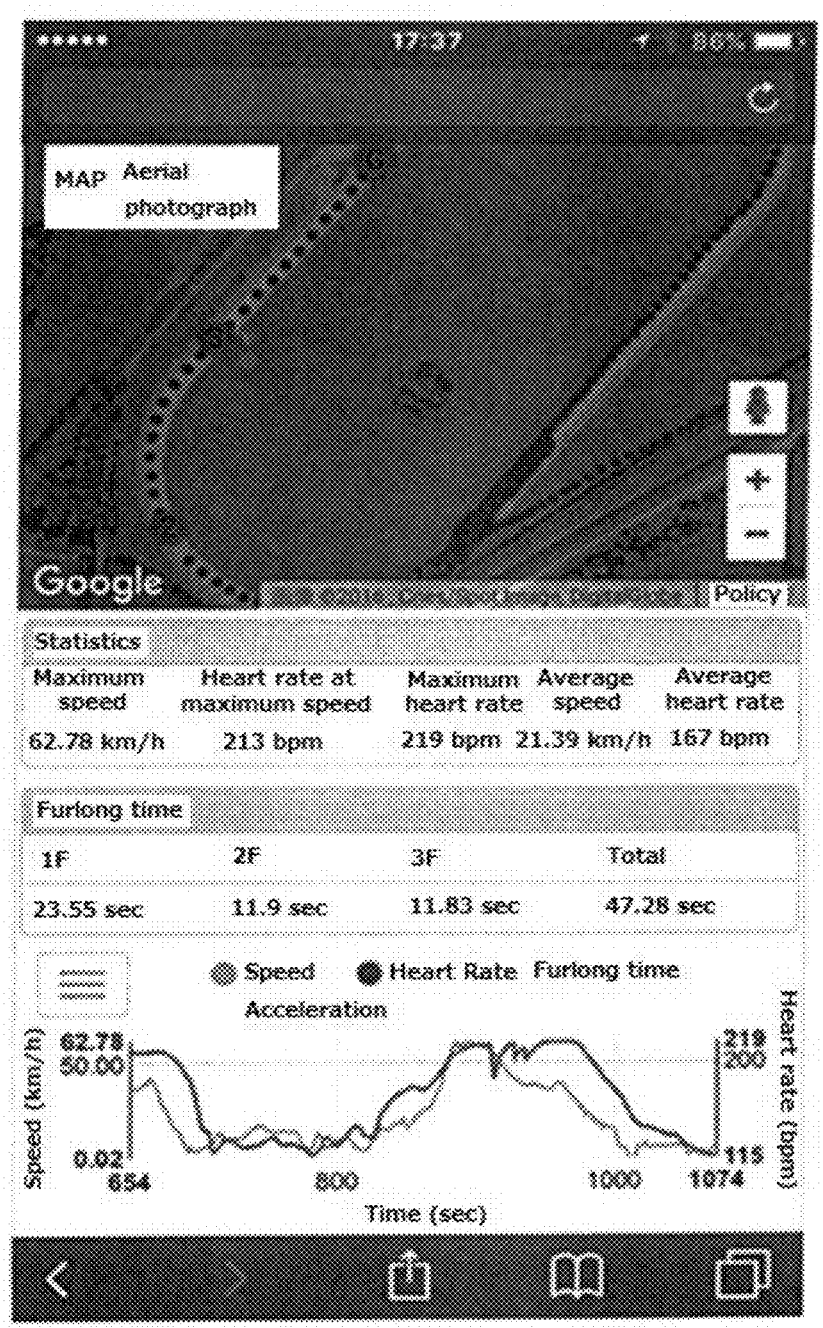

BELT COVER

TECHNICAL FIELD

The present invention relates to a harness for receiving a bioelectric signal of a horse. Specifically, the present invention relates to a belt cover for covering various belts to be attached to the horse, in which the belt cover for receiving the bioelectric signal of the horse can be easily attached to the belt and removed from the belt by incorporating an electrode and an electric wiring into the cover for covering the belt.

BACKGROUND ART

The monitoring of a physical strength of Equidae is extremely important for the confirmation of the health condition and the management of the performance. For example, the sequential monitoring of the bioelectric signal such as a heart rate is useful for the quantitative evaluation of the health conditions.

A system for electronically monitoring a bioelectric signal of a horse during movement has been developed for many years. For example, Patent Documents 1 to 3 propose electrocardiogram monitors for the horse to be attached to a saddle and/or a girth. However, the conventional electrocardiogram monitors have many difficulties with the stable acquisition of a heart rate signal of a horse during the movement, although the conventional electrocardiogram monitors stably can obtain a heart rate signal at the only still state. Therefore, in Patent Documents 1 to 3, the stable signal has been obtained by attaching an electrode for measuring a heart rate signal to both the saddle and the girth. In addition, the stable signal has been obtained by previously wetting a sensor with water in order to improve an electrical adhesion with the body of the horse. However, the stable acquisition of the heart rate signals becomes difficult when the horse exercises at a trot, a canter, and a gallop, and the heart rate signals cannot be stably obtained when the horse takes vigorous exercises such that the horse runs at a top speed in the competition such as a horse race.

In addition, in Patent Documents 1 to 3, multiple electrodes are disposed at sites far away from the body of the horse, and devices for receiving a bioelectric signal to process and transmit the bioelectric signal are also disposed at a site different from the electrode. Thus, there are various problems to be improved such that electric wirings for connecting electrodes with devices for processing and transmitting signals need to be disposed on the body of the horse, the attachment and the removal of complicated device constitutions take much time, and the electric wiring is disconnected during the riding.

Further, Patent Document 4 discloses a heart rate monitor for a horse used in the measurement of the heart rate of the horse at the training. The heart rate monitor comprises an electrode holding member, a pulse transmitter, and a portable pulse receiver.

The electrode holding member includes a holding member main body made of an insulating material to be fixed to the girth, which contains a pair of thin plate-shaped electrode attachment portions that are provided along the inner surface of the girth for fixing the saddle and a transmitter attachment portion that is provided along the outer surface of the girth, a thin plate-shaped electrode having the soft property to be adhered to each electrode attachment portion, a transmitter fixing means fixed to the transmitter attachment portion for fixing the pulse transmitter to the transmitter attachment portion, a conduit body for electrically connecting the signal input terminal of the pulse transmitter fixed by the transmitter fixing means and the corresponding electrode.

Thus, the heart rate monitor disclosed in Patent Document 4 can be easily attached to the horse and removed from the horse. However, in embodiments exemplified in Examples, there is the possibility that a clip used in the electrode holding member is contacted with the body of the horse during activities, and the horse is injured. In addition, the clip is easily disconnected during activities due to unfixed electric wirings, and the troubles are generated easily. Further, when a porous material exemplified as an electrode material is used outdoor, the porous material is easily contaminated by sweat, dust and the like, so that there is the possibility that the cleanliness and hygiene are deteriorated.

PRIOR ART DOCUMENTS

Patent Document

Patent Document 1: U.S. Pat. No. 4,540,001
Patent Document 2: U.S. Pat. No. 4,478,225
Patent Document 3: U.S. Pat. No. 6,504,483
Patent Document 4: Japanese patent No. 3164393

SUMMARY OF THE INVENTION

Problems to be Solved by the Invention

The object of the present invention is to provide a belt cover of the harness in which a system for obtaining a bioelectric signal of the horse containing multiple sensors and processing devices can be easily attached to the horse and removed from the horse, and in which the bioelectric signal can be stably obtained in various exercises of the horse from moderate activities such as a still state and a rest state to vigorous activities such as a run at a top speed.

The present inventors have thought that when all functions required are integrated in the belt cover for covering the belt to be attached to the body of the horse in the process of the development in such a purpose, the belt cover can be easily attached to the horse and removed from the horse. In addition, the electric wiring for connecting electrodes with devices for processing and transmitting signals causes some problems that the connection of the electric wiring becomes troublesome and the electric wiring is disconnected, and that the electric wiring member is contacted with the surface of the body of the horse and the horse is injured in the case where the horse vigorously exercises. Further, the present inventors have found that a communication failure is generated according to a location of the device for communication.

Various belts are used for the harness in order to attach various devices to the body of the horse. The belts include a girth used for attaching a saddle to the body of the horse, a stirrup leather, a bit for attaching reins, a head piece, a brow band, a throat lash, a cheek piece, a nose band, a martingale used for a decoration, a crupper, a belt for attaching a sensor for obtaining biological information, and the like.

When the horse vigorously exercises, the belt often moves on the surface of the body of the horse, the belt scratches the horse, and the horse is injured by the belt in some cases. The belt cover has been attached to the horse in order to resolve such a problem, the scratch between the belt cover and the body of the horse cannot be avoided, and the problem is not solved by only attaching the conventional cover to the belt. Further, as a problem to be noted, when the electrode for obtaining a bioelectric signal is attached to the belt cover, the electrode also moves on the surface of the body of the horse according to the movements of the belt, so that it is difficult to stably obtain the bioelectric signal, and there is a risk that the scratch is generated by contacts among the belt, the electrode, and the body of the horse.

Solutions to the Problems

The present inventors have developed techniques that all functions required for the obtainment of the electrocardiogram information of the horse are integrated to the belt cover for covering the belt to be attached to the horse, the attachment and the removal of the system is simplified to stably obtain the electrocardiogram information, regardless of from the still state to the vigorous exercise. As a result, the present inventors have found that the problem is solved by attaching to the belt cover an electrode capable of stretching according to various curves of the surface of the body of the horse such that the shape change of the body of the horse is followed according to exercises, attaching to the belt cover an electric wiring and a connector for electronically connecting with each elements, and improving the substrate of the belt cover, to complete the present invention.

Specifically, the gist of the present invention is as follows.

[1] A belt cover for attaching to a horse, comprising at least the following (1) to (3):
 (1) an electrode for detecting a bioelectric signal by contacting with the surface of a body of the horse,
 (2) an electric wiring, and
 (3) a connector for connecting with the electric wiring through a part for connecting with the connector and the electric wiring,
 wherein each of the electrode and the electric wiring comprises a stretchable conductor comprising a conductive particle comprising a silver particle and a binder resin,
 the stretchable conductor of the electrode and the electric wiring has a sheet resistance of $0.1\Omega_\square$ or less,
 an insulating layer is laminated on the electric wiring, and
 the electrode and the electric wiring are integrally formed without joints.

[2] The belt cover according to [1], wherein the electrode, the electric wiring, and the part for connecting with the connector and the electric wiring are formed from a stretchable conductor sheet composed of the stretchable conductor.

[3] The belt cover according to [1] or [2], wherein the binder resin comprises a thermoplastic resin, a thermosetting resin, or a rubber, which has a tensile modulus of 1 to 1000 MPa.

[4] The belt cover according to any one of [1] to [3], wherein the silver particle comprises a silver powder like flake or an aggregated silver powder like amorphous.

[5] The belt cover according to any one of [1] to [4], wherein the connector is connected with at least one device selected from any one of the following a) to d):
 a) a device for detecting the bioelectric signal,
 b) a device for memorizing the bioelectric signal to be detected,
 c) a wireless communication device for transmitting the bioelectric signal outside, and
 d) a device for providing a power.

[6] The belt cover according to any one of [1] to [5], wherein the bioelectric signal comprises electrocardiogram waveforms comprising at least heart rate.

[7] The belt cover according to any one of [1] to [6], wherein the electrode is disposed at a distance of 10 cm to 45 cm from the center of a longitudinal direction of the belt cover to the right and left sides, respectively.

[8] The belt cover according to any one of [1] to [7], wherein the connector is disposed at a distance of 1 cm to 25 cm from the center of a longitudinal direction of the belt cover to the right and left sides, respectively.

[9] The belt cover according to any one of [1] to [8], wherein the connector is covered with a cover for the connector and the device so as not to contact with the belly of the horse when the belt cover is attached to the horse.

[10] The belt cover according to any one of [1] to [9], wherein the stretchable conductive sheet constituting the electrode has a thickness of from 0.02 mm to 2.0 am.

[11] The belt cover according to any one of [1] to [10], wherein one electrode has an area of from 20 $cm^2$ to 150 $cm^2$ when contacting with the surface of the body of the horse.

[12] The belt cover according to any one of [1] to [11], wherein a substrate constituting the belt cover comprises a laminate having two or more clothes and an unfixed part is formed between two or more clothes.

[13] The belt cover according to any one of [1] to [12], wherein the belt cover is folded relative to a central axis of a width direction of the belt cover, such that the electrode contacts with the surface of the body of the horse, and the connector and the cover for the connector and the device are disposed on the opposite side to the surface of the body of the horse.

[14] A girth cover for attaching a saddle for riding to a horse, comprising at least the following (1) to (3):
 (1) an electrode for detecting a bioelectric signal by contacting with the surface of a body of the horse,
 (2) an electric wiring, and
 (3) a connector for connecting with the electric wiring through a part for connecting with the connector and the electric wiring,
 wherein each of the electrode and the electric wiring comprises a stretchable conductor comprising a conductive particle comprising a silver particle and a binder resin,
 the stretchable conductor of the electrode and the electric wiring has a sheet resistance of $0.1\Omega_\square$ or less,
 an insulating layer is laminated on the electric wiring, and
 the electrode and the electric wiring are integrally formed without joints.

Effects of the Invention

The electrode for contacting with the surface of a body of a horse of the present invention (hereinafter, simply referred to as electrode in some cases) has a stretchable property, the electrode can be changed to various curve shapes at a three dimension, so that an appropriate contact can be maintained according to the surface of the body of the horse which is changed by the exercises.

It is desirable that the electrode for contacting with the surface of the body of the horse directly contacts with the skin of the horse. However, because the surface of the body of the horse covers with body hairs, it is impossible to directly contact the surface of the electrode with the skin as long as the body hairs are not shaved. Thus, in order to realize the electrical connection between the skin and the surface of the electrode, the electrode used in the conventional system has required additional means that the surface of the body of the horse is wet with water, that is, water is contained in the body hairs, to promote electrical contacts. The electrode used in the present invention has sufficient flexibility and high following properties to the shapes of the body of the horse, and a slight water such as moisture and sweat generated from the surface of the body of the horse is shut between the electrode and the skin even if the body hairs are not wet with water and the like. As a result, the electrocardiogram signals can be detected without the additional means because the body hairs between the electrode and the skin is naturally wet, and effective area of the electrode contacting with the skin becomes large sufficiently.

Even when the horse vigorously exercises, the electric connection between the electrode and the skin can be obtained. For example, when the horse runs at a top speed, it is difficult to obtain the signal because the body hairs wet with intense sweating and the electrode slips on the surface of the body of the horse. However, the electrode used in the present invention can stably obtain a signal because the electrode sufficiently adheres to the body of the horse and effective contacting areas are not changed largely in the case where the electrode slips on the surface of the body of the horse.

In addition, in the present invention, the electric wiring also uses the same stretchable material as the electrode, the electric wiring can stretch according to not only the deformation by the movements of the body of the horse but also the deformation by the expansion of the body by breath, so that the electric wiring can have a minimum length and the belt cover can attach to the horse in a state that the electric wiring is directly bonded to the belt cover (for example girth cover) of the horse. In the cases of electric codes having no stretchable property used in conventional electric wirings and electric wiring containing a conductive fiber, a slack corresponding to the deformation by the expansion of the body is required, the electric wiring having the slack is caught by other harness or the jockey who gets on and off, so that the electric wiring is easily disconnected. In addition, when the electric wiring has a minimum length without the slack, the electric wiring enters the body of the horse, and the horse is injured by the scratch between the body of the horse and the electric wiring during the vigorous exercises. At this time, the horse cannot indicate the intention with the language and the state that the equipment enters the body will be discomfort for the horse.

On the contrary, by using the belt cover (for example girth cover) of the present invention, a heart rate and an electrocardiogram waveform can be measured correctly and stably according to any movements of the body of the horse from the stationary state to the trot, the gallop. Therefore, the strength of the appropriate training is derived and the optimized training can be managed while the heart rate and other bioelectric signal are compared with the location information and the strength of the exercise obtained from the speed at the exercise. Further, the health of the body of the horse can be administrated by early finding limp, disease and insufficient physiological capacity from the abnormal bioelectric signals.

In the present invention, the stable communication can be obtained by disposing the communication function at a location satisfying a given condition, so that the electrocardiogram information of the horse can be received and grasped at a remote monitoring. The technique of obtaining the electrocardiogram information at the remote monitoring has been known previously.

However, the horse becomes large dielectric comparing with the human, and serves as a wave absorber for the communication. Thus, at transmission, a power for canceling energy absorbed by the horse is required, and at reception, the system requires the reception property at high sensitivity taking consideration into the signal attenuation from the energy absorbed by the horse. Therefore, a power unit requires a primary cell or a secondary cell having a relatively large size, and in such a case, the weight of the whole system becomes heavy and the burden to the horse becomes large.

Further, importantly, there are the similar problems that the electric wiring enters the body of the horse and the horse is injured by the scratch between the electric wiring and the body since the bumps and dents on the equipment are generated by the shapes of the secondary cell. However, in the present invention, this problem is not generated because the device can be disposed at a location exhibiting good transmission and reception efficiency, the power consumption can be minimized, and the power unit of the system can be miniaturized.

The harness is always exposed to the sweat by the horse and contacts with waste products in some cases, so that the harness requires the durability to a horse body fluid such as sweat and to frequent washing and laundering. Copper wiring used in the common electric wiring, a conductive fiber plated with copper and nickel, a surface-treated chemically synthetic fiber with copper complex, a conductive polymer are impaired in the conductive function by a salt component contained in the sweat, an ammonia component generated by the decomposition of the urea contained in the sweat, a surfactant contained in the detergent and the like. However, the stretchable conductors used in the electrode and the electric wiring of the present invention have high durability to these requirements and can be used repeatedly.

Thus, the stretchable conductor used in the present invention contains a metal component as a conductive component, and the alkaline components such as the salt component and the ammonia component can have an influence on the stretchable conductor. However, surprisingly, the present inventors have found that the stretchable conductor practically exhibits sufficient durability. The present inventors have presumed that, even when insulating membranes such as membranes of metal oxide and metal hydroxide are formed on the surface of the metal component due to the alkaline components, this effect generates because the insulating membrane formed on the surface is removed by scratching the metal component according to the stretch of the conductive membrane.

In the present invention, a silver particle is mainly used as a conductive component of the stretchable conductor. The silver is known as not only good conductors but also materials having an antibacterial action. In the case where the product contacts with a living body and the product is used in outdoor as applications of the present invention, the bacteria adheres to the product and the mold is generated in same cases. However, in the present invention, a biologically clean state can be kept by the antibacterial action of the silver without using a disinfectant and a germicide.

In the preferred embodiment of the present invention, a substrate constituting the belt cover (for example girth cover) comprises a laminate having two or more clothes and an unfixed part is formed between two or more clothes. In this case, the cloth contacting with the belt and the cloth contacting with the body of the horse in the belt cover have independently flexibility, so that a gap generated by relative movement between the belt and the body of the horse can be substituted with a gap between clothes constituting the belt cover. By the effects, the scratch between the belt cover and the body of the horse can be minimized, while the stable contact between the electrode and the body of the horse can be realized together with the prevention of the injury of the body of the horse.

The belt cover of the present invention can be applied to various belts in the case where the human rides on the horse and the case where the human does not ride on the horse, and various sensors and equipment required in the sensors can be attached to various belts.

BRIEF EXPLANATION OF DRAWINGS

FIG. 1 is one example of photograph in which the jockey rides on the horse having the saddle attached using the belt.

FIG. 2 is one example of the belt.

FIG. 3 is one example of the belt cover of the present invention.

FIG. 4 is one example of a magnified view of the center in the longitudinal direction of the belt cover in the case where the belt cover of the present invention is folded along with the center axis of the width direction.

FIG. 5 is a graph containing a heart rate and a speed which are measured during training from the trot to the gallop using the belt cover of the present invention.

MODES FOR CARRYING OUT THE INVENTION

A belt cover (for example a girth cover) of the present invention is a belt cover for attaching to a horse (for example a girth cover for attaching a saddle for riding to the horse), the belt cover comprises at least (1) an electrode for detecting a bioelectric signal by contacting with the surface of a body of the horse, (2) an electric wiring, and (3) a connector for connecting with the electric wiring through a part for connecting with the connector and the electric wiring, wherein each of the electrode and the electric wiring comprises a stretchable conductor comprising a conductive particle comprising a silver particle and a binder resin, the stretchable conductor of the electrode and the electric wiring has a sheet resistance of $0.1\Omega_\square$ or less, an insulating layer is laminated on the electric wiring, and the electrode and the electric wiring are integrally formed without joints.

The phrase "integrally formed without joints" means that a connection between the electrode and the electric wiring is not formed, and the electrode and the electric wiring are continuously formed except that an insulating layer is formed on the electric wiring.

In the case where the electrode and the electric wiring are integrally formed without joints, both the electrode and the electric wiring can be changed according to the movements of the horse. As a result, various physical activities of the horse can be traced without having the influence on the physical movements. In addition, the integration of the electrode and the electric wiring prevents the electric wiring from removing during the physical activities and the belt cover containing the electrode and the electric wiring can be washed as it is after use. Further, the water does not invade the connection between the electrode and the electric wiring, so that the physical activities of the horse can be traced even when the horse sweats much and the horse runs in the rain.

The belt cover of the present invention preferably comprises a stretchable conductive sheet containing at least the electrode and the electric wiring, and more preferably comprises a stretchable conductive sheet containing at least the electrode, the electric wiring, and a part connecting to the connector (the part for connecting with the connector and the electric wiring). According to the stretchable conductive sheet, there is a merit that the electrode, the electric wiring, and the part connecting to the connector can be prepared at the same time. The stretchable conductive sheet may be one layer or two or more layers.

In the present invention, the horse is a general term of the animal containing Equidae of Perissodactyla, *Equus*. The *Equus* belonging to Equidae includes nine kinds of subgenus *Equus* such as light breed horses such as thoroughbred, Anglo-Arab, Arab; heavy breed horses such as Percheron, Breton; intermediate species such as Hanovar, Westfalen, Quarter horse; *Equus caballus* (domestic horses) such as japan native species such as Kiso horse, Mongolian horse, Asinus such as *Equus asinus* (domestic species), *Equus africanus*, *Equus hemionus* such *Equus hemionus*; *Equus kiang*, Hippotigris such as *Equus zebra*, *Equus quagga*, Dolichohippus such as *Equus grevyi*. In addition, Mule crossbreeded by male *Equus asinus* and female horse, Hinny crossbreeded by male horse and female *Equus asinus*, Zorse crossbreeded by male zebra and female horse, Zeedonk or Zoney crossbreeded by *Equus asinus* and Hoppotigris, Zony crossbreeded by male Hoppotigris and female pony, zebroid crossbreeded by Hoppotigris and many species are known as crossbreeds, and these are called as horse in the present invention.

The present invention encompasses a belt cover for covering a belt to be attached to the horse. The belt to be attached to the horse includes a girth used for attaching a saddle to the horse, a stirrup leather, a bit for attaching reins, a head piece, a brow band, a throat lash, a cheek piece, a nose band, a martingale used for a decoration, a crupper, a belt for attaching a sensor for obtaining biological information to the horse, and the like.

The belt cover utilized in the present invention is preferably a cover for covering the girth used in the purpose of riding on the horse, or, fixing a saddle for the horse riding to the horse. The combination of the saddle for the horse riding, the girth, and the girth cover is used in various situations such as a horse racing, an equestrian event, a polo, a recreation, a riding event, a movie, a historical film, a western film, and the like.

FIG. 1 is one example of the belt (for example girth) for fixing a saddle to the horse, the belt is shown as sign 3 in FIG. 1. One example of the belt (for example girth) is shown in FIG. 2. Many girths have the rigid property on the surface because the girth is a solid belt for tightly fixing a saddle on the horse.

The belt (for example girth) is preferably a material having a rigid property than that of a belt cover (for example girth cover) as set forth below.

The material of the belt includes a fabric, a knitting, a woven fabric, a rubber, a plastic, a synthetic leather, a natural leather, and the like.

As shown in FIG. 2, metal fittings to be connected to the saddle may be disposed on both edges of the belt (for example girth).

The belt cover is often used to prevent the hard girth from contacting the horse body to injure the horse. The belt cover covers the belt using more soft materials than the common belt material and avoids the direct contact of the horse body and the belt. The shape of the belt cover may be any one as long as this purpose is achieved and the belt cover has a cylinder shape or a rectangular shape. When the belt cover has the rectangular shape, the belt cover may be used to wind on the belt or each of narrow sides of the belt cover is adjusted to have a length of one round of the belt and connecting parts such as a bouton, a hook and loop fastener (for example hook and loop fastener 12 in FIG. 3), and a zipper are attached along with the long side of the belt cover, the long sides of the belt cover are bonded each other to make a cylinder shape before the belt cover is attached to the belt. In the present invention, the belt cover having the rectangular shape and connecting parts to be attached along with the long side are preferably used due to simple attachment and removal.

The material of the belt cover of the present invention, that is, the substrate of the belt cover is preferably a cloth (including a non-woven fabric), a fabric, and a knitting. In addition, the material of the belt cover preferably has stretch properties to same degree and the material of the belt cover has an elongation of preferably 3 to 80%, more preferably 10 to 50%, and even preferably 15 to 30% in a given direction.

Thus, the belt cover having a soft material such as a fabric, a knitting, a non-woven fabric can be used. In addition, the material (particularly knitting) having an elasticity in a direction of the thickness is preferably used to improve the adhesion of the electrode and the horse.

For example, those laminating the fabric or the knitting with materials having an elasticity such as rubber materials, urethane forms and the woven fabrics are more preferred. Concretely, those laminating the urethane form on one side of the fabric or the knitting and those sandwiching neoprene rubber between two fabrics or knittings are preferably used.

The belt cover (for example girth cover) may have a thickness of 0.4 mm to 50 mm. The belt cover has a thickness of preferably 0.7 mm to 35 mm, more preferably 1.0 mm to 25 mm, even preferably 1.0 mm to 10 mm, and even more preferably 1.0 mm to 5 mm. In the case of less than 0.4 mm, gaps between the horse and the belt cover are easily formed, and the adhesion between the attached electrode and the horse is easily decreased. In the case of more than 50 m, the thickness of the belt cover becomes thicker, and the saddle is hardly fixed.

The belt cover (for example girth cover) has a length of for example, 50 cm to 2 m, and preferably 70 cm to 1.5 m.

The belt cover (for example girth cover) has a width of for example 10 cm to 60 cm, and preferably 15 cm to 40 cm.

The base materials of the belt cover (for example girth cover) of the present invention is preferably a laminate having two or more clothes. In addition, it is preferable that an unfixed part is formed between two or more clothes constituting the laminate. The laminate having two or more clothes and un-fixed parts between the clothes means those surrounding the belt with two or more clothes when the belt cover is attached to the belt. The two or more clothes can be fixed with sewing or adhesion such as a hot melt adhesive. In the present invention, it is preferable that outer peripheries of the belt cover are sewed without sewing or bonding center parts of the belt cover, the center parts are maintained at a naturally stacking state.

By using such a laminate, even if the belt moves according to exercise of the horse, the belt cover is not followed by the belt, the electrode for contacting with the body of the horse and the electric wiring on disposed on the belt cover are fixed as it is, so that the exercise of the horse can be traced.

<Electrode, Electric Wiring, Connector Connecting Part, and Connector>

In the present invention, it is preferable that at least a pair of electrodes is attached to a belt cover (for example girth cover), it is more preferable that at least a pair of electrodes is attached to a center of the belt cover, and it is even preferable that at least a pair of electrodes is attached at a symmetry location to the center of the belt cover.

In order to correctly sense heart rates, it is preferable that the electrode for contacting with the surface of the body of the horse is disposed a position apart from the center of a longitudinal direction of the belt cover to the right and left sides, respectively, on the belt cover (for example girth cover) facing to the surface of the body of the horse such that the heart is sandwiched by the electrodes. Concretely, the electrode for contacting with the surface of the body of the horse is disposed at a distance of preferably 10 cm to 45 cm, more preferably 20 cm to 40 cm from the center of a longitudinal direction of the belt cover to the right and left sides, respectively. When the electrode is disposed at a distance less than 5 cm from the center, the potential difference from the electrocardiograph is hardly detected due the close detection positions. In addition, when the electrode is disposed at a distance of more than 50 cm, the noise of electromyography generated in each parts of the body of the horse becomes large and the electrocardiograph measurement becomes difficult. Further, when the electrode is disposed at a distance of more than 50 cm, the electrode is close to the saddle and the electrode is easily broken by mechanical stresses and the like in same cases. The position of the electrode is based on the center of gravity of each electrodes. In the present invention, the belt cover is attached to the belt such that the center part of a longitudinal direction of the belt cover is adjusted to the center or its vicinity of the body of the horse (the belly or the vicinity of the belly nearest the ground). In this case, the position of the electrode may be adjusted based on the center of the longitudinal direction of the belt cover.

One electrode for contacting with the surface of the body of the horse has an area of preferably 20 $cm^2$ to 150 $cm^2$, more preferably 25 $cm^2$ to 120 $cm^2$, and even preferably 30 $cm^2$ to 100 $cm^2$. When the area is less than 20 $cm^2$, the acquisition of the bioelectric signal of the horse becomes difficult in some cases.

It is preferable that the electrode and the electric wiring of the present invention are formed without joints, and it is more preferable that the electrode, the electric wiring and the connector connecting part (the part for connecting with the connector and the electric wiring) are formed without joints.

The stretchable conductor used in the electrode, the electric wiring, the connector connecting part of the present invention is different from conductive yarns and copper foils, and both the electrode and the electric wiring having softness and stretchable property can be constituted without joints using only one material. As a result, the unnatural roughness is not formed on the side contacting with the body of the horse, the burden on the body of the horse is reduced, so that the injury of the body of the horse can be prevented.

It is preferable that a connector is disposed on the connector connecting part. Preferably, the connector is connected with at least one device selected from any one of a) a device for detecting the bioelectric signal, b) a device for memorizing the bioelectric signal to be detected, c) a wireless communication device for transmitting the bioelectric signal outside, and d) a device for providing a power. The at least one device is referred to as "device" or "processing equipment" for simplification. The device having such a function may be those conventionally known and include processing equipment such as a signal processing processor, a primary and secondary memorizing device, a GPS receiver, an antenna, a power supply and the like. The bioelectric signal preferably comprises electrocardiogram waveforms comprising at least heart rate.

A snap button (hook) made from metals can be used to the connector of the present invention. The use of the snap button is only one example and known connectors also are used. In the case of the non-contact bonding, a plane coil or a plane electrode can be utilized as a signal supply side. These can be simply prepared using the stretchable conductor of the present invention. Known means such as a caulking, a conductive adhesive, a soldering at a low temperature, a sewing by a conductive yarn can be used to the connection with the connector. The connection means is used in multiple combinations in the view of the reliability. Preferably, the connector is covered with the cover for the connector and the device so as not to contact with the belly of the horse when the belt cover is attached to the horse.

FIG. 3 is one example indicating a belt cover (for example girth cover) 5 containing a pair of electrodes 6, a connector connecting part 11 using a pair of snap buttons (in FIG. 4, the electric point of the connector is snap button 9), an electric wiring 7 connecting the electrode and the connector. In FIG. 3, the cover 8 for the connector and the device is closed to protect the device and the connector may be covered. FIG. 4 is a partially magnified drawing indicating that the cover for the connector and the device is open. The cover can be closed with hook and loop fastener 10 and removed from hook and loop fastener 10. The processing device is connected with two electrodes 6 through the electric wiring 7 integrally formed with the electrode.

FIG. 3 and FIG. 4 indicate one example that the electrodes, the electric wirings, and the connectors constitute a pair one by one, while the electric wiring, the electrode, and the connector may be combined in the multiple number in order to ensure electrical needs or the redundancy of the electric wiring, if necessary. FIG. 3 and FIG. 4 indicate one example that the electrode and the processing device are connected by direct contact, while the electrode and the processing device may be connected by non-direct contact such as the capacitive coupling or the inductive coupling.

It is preferable that the belt cover (for example girth cover) is folded relative to a central axis of a width direction of the belt cover, such that the electrode contacts with the surface of the body of the horse, and the connector and the cover for the connector and the device are disposed on the opposite side to the surface of the body of the horse. Concretely, in FIG. 3, the belt cover is folded at a mountain fold along with the center axis of the width direction (the central axis is indicated by arrow in FIG. 3), the electrode is disposed on the body of the horse, the connector and the cover for the connector and the device are disposed on the opposite side of the body of the horse. In this case, the electric wiring constituted by the stretchable conductor is not broken by folding and can transmit the bioelectric signal from the electrode to the connector side.

<Processing Device>

The processing device may be connected with the belt cover of the present invention. The processing device is an electric equipment having functions of measurement, memory, operation, communication of the detected electric signal through the electrode. The electric equipment measures heart rates, fluctuation patterns of the heart rate, electrocardiographic waveform, integrates these and position display signals received from GPS system, and transmits the integrated information outside. In the present invention, positions for attaching the processing device are prepared in given parts of the belt cover, and systems for managing bioelectric information can be constituted without requiring complicated electric wirings.

In addition, the processing device can be simply attached to the belt cover and removed from the belt cover by making the connecting parts of the belt cover a detachable structure. By this, the processing device is removed from the belt cover, the processing device can be subjected to the maintenance, the charge, the battery replacement, the repair and the like, the belt cover of which the belt, the electric wiring, and the electrode are integrally formed can be washed to keep cleanliness. The detachable connecting part means that spring hooks (female hooks) are attached to connectors (electric points), spring hooks (male hooks) are attached to electric points of the processing device, the processing device can be simply attached and removed by the attachment and the removal of the female spring hooks and the male spring hooks. In the case using spring hooks, there is a merit that other fiber articles and washing machines are hardly damaged by the spring hooks because the spring hooks are easily installed and removed, and the spring hooks have the durability to repeated installation, removal and wash. However, in the present invention, the connecting part is not limited to the spring hook, and other button contacts and other connectors may be used. Any connector can be used as long as the connector has a conductivity capable of passing the bioelectric signal and the connector can be installed and removed.

In the present invention, the processing device has the communication function, the positions of the processing device to be attached may be provided with the side contacting with outside air when the belt cover is attached to the belt. In the present invention, the connectors (electric contacts) can be used in two or more pieces, in the case of two connectors, a midpoint of a line segment connecting between the connectors is set as a center of the connectors, in the case of three or more connectors, a midpoint of a line segment connecting among three connectors or a gravity of a polygon connecting three connectors is set as a center of the connectors.

The connector (preferably the center of the connector) is disposed at a distance of preferably 1 cm to 25 cm, more preferably 1 cm to 20 cm from the center (the center part of the belly of the horse (the belly nearest to the ground) of a longitudinal direction of the belt cover (for example girth cover) in the case where the belt does not have asymmetry shape) to the right and left sides, respectively. It is even preferable that the center of the connector disposed along with the longitudinal direction of the belt cover (for example girth cover) is disposed at a distance of 1 cm to 7 cm from the center of the longitudinal direction of the belt cover. In the case where the connectors are used as a pair of electric contacts or two electric contacts, it is even preferable that one electric contact is disposed at a distance of 1 cm to 7 cm from the center of the longitudinal direction of the belt cover, while other electric contact is disposed at a distance of more than 7 cm and 15 cm or less from the center of the longitudinal direction of the belt cover. When two electric contacts are disposed at a left side from the center of the longitudinal direction of the belt cover, the center of the connectors also are disposed at a left side from the center of the longitudinal direction of the belt cover.

When the electric contacts are disposed like this, the body of the horse is not injured and the processing device is not broken by contacting the front leg with the processing device at even gallop. Since the body of the horse is a giant wave absorber, troubles are generated in the reception of the GPS signals when the communication device is located beneath the body of the horse. The processing device attached to a given position is housed in the belt cover provided with a pocket or a pouch, and this can prevent the processing device from disconnecting, breaking, or malfunctioning by the shock and the contact during the riding. In one preferred embodiment of the present invention, a removable protect cover for the processing device is provided with the hook and loop fastener.

<Characteristics of Materials Used in Electrode, Electric Wiring, and Connector Connecting Part>

Hereinafter, the stretchable conductor used for the electrode, the electric wiring, and the connector connecting part of the present invention is explained. The stretchable conductor of the present invention is a stretchable conductive layer or a stretchable conductor sheet having a sheet resistance (preferably initial value of the sheet resistance) of 0.1 $\Omega_\square$ or less. The sheet resistance can be measured according to the following formula.

Sheet resistance [$\Omega_\square$]=resistivity [$\Omega$cm]/sheet thickness [cm]

When the sheet thickness is 100 μm (0.01 cm), the stretchable conductor requires the resistivity of $1\times10^{-3}$ $\Omega$cm or less to satisfy the sheet resistance of $0.1\Omega_\square$ or less in the conductive material.

The stretchable conductive layer (stretchable conductive sheet) containing the electrode, the electric wiring, and the connector connecting part has a thickness of preferably 0.02 mm to 2.0 mm, more preferably 0.03 mm to 1.5 mm, even preferably 0.05 mm to 1.0 mm, and even more preferably 0.05 mm to 0.5 mm. When the stretchable conductive sheet does not satisfy the thickness of the above range, the durability to the repeated stretch and the scratch is decreased in same cases. In addition, when the stretchable conductive sheet has the thickness beyond the above range, steps between a part having the electrode and the electric wiring and a part without having the electrode and the electric wiring become large, and the horse is injured by scratch in some cases.

The stretchable conductive layer of the present invention may have the stretchable property. The stretchable property means that the conductivity of the stretchable conductive layer is maintained even if the layer is repeatedly stretched by 10% or more 100 times. It is preferable that the stretchable conductive layer of the present invention has a fracture elongation of 50% or more. Further, it is preferable that the stretchable conductive layer of the present invention has a tensile modulus of 10 to 500 MPa. Such a stretchable conductive layer having the stretchable property may be formed from a stretchable conductive composition.

The stretchable conductive composition can be obtained from a stretchable conductive paste as set forth below. The stretchable conductive paste as one means of the constitution of the present invention is explained as follows. The stretchable conductive paste contains at least a conductive particle, a stretchable resin, a solvent and a non-conductive particle to be added if necessary.

The conductive particle of the present invention contains a material having a resistivity of $1\times10^{-1}$ $\Omega$cm or less and a particle diameter of 100 μm or less. The material having a resistivity of $1\times10^{-1}$ $\Omega$cm or less includes metals, alloys, carbon, doped semiconductors, conductive polymers, and the like. The preferred conductive particle used in the present invention includes particles made from metals such as silver, gold, platinum, palladium, copper, nickel, aluminum, zinc, lead, tin; particles made from alloys such as brass, bronze, cupronickel, solder; hybrid particles made from copper coated with silver; polymer particles plated with metals, glass particles plated with metals, ceramic particles coated with metals, and the like.

The conductive particle of the present invention is preferably a silver powder like flake or an aggregated silver powder like amorphous as a main component. The main component means that the conductive particle is used in an amount of 90% by mass or more per 100% by mass of the conductive particle. The aggregated silver powder like amorphous is powder of which a primary particle having a cube shape or an amorphous shape is aggregated at the three dimension. The aggregated silver powder like amorphous or the silver powder like flake is preferable because these has a large specific surface area than cube silver powder and these can form a conductive network at a small filler content. The aggregated silver powder like amorphous is more preferable because this easily forms a conductive network due to non-monodisperse and the physical contacts among the particles.

The particle diameter of the silver powder like flake is not limited particularly, and the silver powder like flake has an average particle diameter (50% D) of preferably 0.5 to 20 μm, and more preferably 3 to 12 μm, as measured with a dynamic light scattering method. In the case of more than 20 μm, the fine electric wiring is hardly formed, clogging of screen printing is generated. In the case of less than of 0.5 μm, the particles of the silver powder like flake cannot be contacted each other in the low filling, and the conductivity becomes worse in same cases.

The particle diameter of the aggregated silver powder like amorphous is not limited particularly, and an average particle diameter (50% D) of the aggregated silver powder like amorphous is preferably 1 to 20 μm, and more preferably 3 to 12 m, as measured with the dynamic light scattering method. When the average particle diameter is more than 20 μm, the preparation of the paste becomes difficult due to the decrease of the dispersibility. When the average particle diameter is less than 1 μm, conductive effects of the aggregated silver powder are lowered, and the conductivity cannot be maintained in the case where the aggregated silver powder is filled in a small amount.

An amount of the conductive particle is for example, 30 to 90% by mass, preferably 40 to 80% by mass, and even preferably 50 to 70% by mass per 100% by mass of a total of the conductive particle, the stretchable resin, and the non-conductive particle to be added if necessary.

The non-conductive particle of the present invention may be a particle composed of an organic or inorganic insulating material. Among these, the particle composed of the inorganic insulating material is preferred. The particle composed of the inorganic material is added in order to improve the printing property, the stretching property, and the surface property of the coating. The non-conductive particle includes an inorganic particle such as barium sulfate, silica, titanium oxide, talc, alumina; organic particle such as a micro gel composed of a resin and the like.

In the present invention, the non-conductive particle is preferably a barium sulfate particle. The barium sulfate particle can include elutriated barium sulfate particle which is pulverized product of barite mineral called as natural barite and precipitated barium sulfate particle prepared by a chemical reaction. In the present invention, the precipitated barium sulfate particle is preferably used due to easy control of the particle diameter. The barium sulfate particle has an average particle diameter of preferably 0.01 to 18 μm, more preferably 0.05 to 8 μm, even preferably 0.2 to 3 μm as measured by a dynamic light scattering method. In addition, it is preferable that the barium sulfate particle is surface-treated with hydroxide and/or oxide of Al, Si, or Al and Si. By the surface treatment, the hydroxide and/or oxide of Al, Si, or Al and Si is precipitated on the surface of the barium sulfate particle. The amount to be precipitated is preferably 0.5 to 50, more preferably 2 to 30, per 100 of barium element in an element ratio calculated according to fluorescent X-ray analysis.

The non-conductive particle (preferably barium sulfate particle) preferably has a smaller average particle diameter than that of the conductive particle. The conductive particle has an average particle diameter of preferably 1.5 times or more, more preferably 2.4 times or more, and even preferably 4.5 times or more than that of non-conductive particle (preferably barium sulfate particle). When the non-conductive particle (preferably barium sulfate particle) has an average particle of more than the above range, the roughness of the surface of the coating becomes large, the coating is easily broken at the extension. On the other hand, when the non-conductive particle (preferably barium sulfate particle) has an average particle of less than the above range, effects of improving durability to stretch becomes small, a viscosity of the paste becomes high, and the preparation of the paste becomes difficult.

An amount of the non-conductive particle (preferably barium sulfate particle) of the present invention is for example 2 to 30% by mass, preferably 3 to 20% by mass, and more preferably 4 to 15% by mass per a total of the conductive particle and the non-conductive particle (preferably barium sulfate particle). When the amount of the non-conductive particle (barium sulfate particle) is beyond the above amount, the conductivity on the surface of the coating is decreased. On the other hand, when the amount of the non-conductive particle (preferably barium sulfate particle) is smaller than the above amount, effects of improving durability to stretch are hardly exhibited.

The stretchable resin (referred to as binder resin) of the present invention includes a thermoplastic resin, a thermosetting resin, or a rubber, which has a tensile modulus of 1 to 1000 MPa. The stretchable resin is preferably a rubber in the viewpoint of the stretchable property of the film. The rubber includes a urethane rubber, an acrylic rubber, a silicone rubber, a butadiene rubber, a nitrile group-containing rubber such as a nitrile rubber, a hydrogenated nitrile rubber, a chloroprene rubber, an isoprene rubber, a vulcanized rubber, a styrene butadiene rubber, a butyl rubber, a chlorosulfonated polyethylene rubber, an ethylene propylene rubber, a fluorinated vinylidene copolymer and the like. Among these, the nitrile group-containing rubber, the chloroprene rubber, the chlorosulfonated polyethylene rubber are preferable, and the nitrile group-containing rubber is particularly preferably. The stretchable resin has a tensile modulus of preferably 3 to 600 MPa, more preferably 10 to 500 MPa, and even preferably 30 to 300 MPa.

The nitrile group-containing rubber may be a rubber or an elastomer containing a nitrile group without limiting particularly. The nitrile group-containing rubber is preferably nitrile rubber and hydrogenated nitrile rubber. The nitrile rubber is preferably a copolymer of butadiene and acrylonitrile. When an amount of the nitrile to be bonded is large, the affinity with the metal increases and the rubber elasticity contributing to the stretch decreases. Therefore, an amount of the acrylonitrile to be bonded is preferably 18 to 50% by mass, and particularly preferably 40 to 50% by mass per 100% by mass of the acrylonitrile butadiene copolymer rubber.

In the present invention, an amount of the stretchable resin is for example, 7 to 35% by mass, preferably 9 to 28% by mass, and even preferably 12 to 20% by mass per 100% by mass of a total of the conductive particle, the stretchable resin, and the non-conductive particle to be added if necessary.

In addition, an epoxy resin may be added to the stretchable conductive paste of the present invention. The epoxy resin of the present invention is preferably bisphenol A type epoxy resin or phenol novolac type epoxy resin. When the epoxy resin is compounded, a curable agent of the epoxy resin can be compounded to the epoxy resin. As the curable agent, known amine compounds, polyamine compounds, and the like may be used. The curable agent is compounded in an amount of preferably 5 to 50% by mass, and more preferably 10 to 30% by mass per 100% by mass of the epoxy resin. The epoxy resin and the curable agent are compounded in an amount of for example 3 to 40% by mass, preferably 5 to 30% by mass, and more preferably 8 to 24% by mass per 100% by mass of a total resin including the stretchable resin.

The stretchable conductive paste of the present invention may contain a solvent. The solvent of the present invention is water or an organic solvent. An amount of the solvent is appropriately adjusted according to a viscosity required in the stretchable conductive paste without limiting particularly. The amount of the solvent is preferably 30 to 80 parts by mass per 100 parts by mass of a total of the conductive particle, the non-conductive particle (preferably barium sulfate particle), and the stretchable resin.

The organic solvent used in the present invention has a boiling point of preferably 100° C. or more and less than 300° C., more preferably 130° C. or more and 280° C. or less. When the organic solvent has a lower boiling point, the solvent evaporates in the step of preparing the paste and the use of the paste and a ratio of components constituting the stretchable conductive paste is changed in same cases. On the other hand, when the organic solvent has a high boiling point, the solvent is left in a large amount in the coating after drying and curing, and the reliability of the coating is lowered in same cases.

The organic solvent of the present invention includes cyclohexanone, toluene, xylene, isophorone, γ-butyrolactone, benzylalcohol, SOLVESSO™ 100, SOLVESSO™ 150, SOLVESSO™ 200 (manufactured by Exxon mobil chemical), propylene glycol monomethyl ether acetate, terpineol, butylglycol acetate, diamylbenzene, triamylbenzene, n-dodecanol, diethylene glycol, ethylene glycol monoethylether acetate, diethylene glycol monoethyl ether acetate, diethylene glycol monobutyl ether acetate, diethylene glycol dibutyl ether, diethylene glycol monoacetate, triethylene glycol diacetate, triethylene glycol, triethylene glycol monomethyl ether, triethylene glycol monoethyl ether, triethylene glycol monobutyl ether, tetraethylene glycol, tetraethylene glycol monobutyl ether, tripropylene glycol, tripropylene glycol monomethyl ether, 2,2,4-trimethyl-1,3-pentanediol monoisobutyrate, and the like. In addition, petroleum hydrocarbons include AF solvent No. 4 (boiling point: 240° C. to 265° C.), AF solvent No. 5 (boiling point: 275° C. to 306° C.), AF solvent No. 6 (boiling point: 296° C. to 317° C.), AF solvent No. 7 (boiling point: 259° C. to 282° C.), solvent H No. 0 (boiling point: 245° C. to 265° C.) (manufactured by JXTG Nippon Oil & Energy Corporation, formerly, SHIN-NIHON SEKIYU Co., Ltd), and the like. These may be used in two or more kinds if necessary. Such an organic solvent is contained in an appropriate amount such that the stretchable conductive paste has a viscosity appropriate for printing.

The stretchable conductive paste of the present invention can be obtained by mixing and dispersing a conductive particle, a non-conductive particle (preferably barium sulfate particle), a stretchable resin, a solvent with dispersers such as a dissolver, a three roll mil, a planetary centrifugal mixer, an attritor, a ball mil, and a sand mill.

Known organic and inorganic additives for the provision of the printing property, the adjustment of the color tone, the leveling, the antioxidation, and the UV absorption can be added to the stretchable conductive paste of the present invention as long as the effect of the present invention is not impaired.

The stretchable conductor of the present invention may be formed with the stretchable conductive paste in a given pattern using printings such as screen printing, gravure printing, ink jet printing, and offset printing. The printing may be directly made on the substrate and the printing may be made on the insulating underlayer formed on the substrate if necessary. Further, patterns printed in a release film as an intermediate medium can be transferred to the substrate.

In the present invention, the stretchable conductive sheet can be prepared by using a method for coating a stretchable conductive paste on the supporting film using die-coating, squeegee coating, comma coater, gravure coater, and the like, drying the stretchable conductive paste on the supporting film to prepare a stretchable conductive sheet, cutting the stretchable conductive sheet in a given pattern, and laminating the resultant stretchable conductive sheet on the substrate. A method for obtaining the stretchable conductive sheet includes a method for mixing and melting components obtaining by subtracting a solvent component from the stretchable conductive paste at a high temperature to prepare a conductive compound, and molding the conductive compound to prepare a stretchable conductive sheet using a method such as an extruding film formation. The stretchable conductive sheet may be bonded to the substrate using an adhesive. Practically, the adhesive is preferably a hot melt adhesive.

The insulating layer is disposed on the electric wiring of the present invention. The insulating layer of the present invention is a layer for insulating at least the surface side of the electric wiring, and preferably a layer for insulating the surface side and the back side electric wiring. In the case where the insulating layer is disposed on the back side of the electric wiring, the insulating layer can serves as an underlayer or an adhesive layer with the substrate. The insulation encompasses a mechanical insulation, a chemical insulation, and a biological insulation in addition to the electric insulation, and means a function for insulating a conductive layer from water passing through the substrate, chemical substances, and biological matter.

The insulating layer of the present invention preferably composed of a soft polymer. The soft polymer can include a rubber, and an elastomer. The rubber and the elastomer include resins for forming the conductive layer, and a hot melt urethane, a polyurethane and the like can be used preferably.

The insulating layer of the present invention preferably has the stretchable property in which 10% or more of stretch can be repeated. In addition, the insulating layer of the present invention preferably has a tensile elongation of 50% or more. Further, the insulating layer of the present invention preferably has a tensile modulus of 10 to 500 MPa.

The insulating layer of the present invention is preferably applied to the substrate through a liquid or a slurry such as a coating solution, a dipping solution, an ink for printing, a paste for printing. The liquid or the slurry may be obtained by dissolving and dispersing the materials for the insulation in a solvent. In order to control the printability, the formulation of known leveling agents and thixotropic agents is encompassed in the present invention. The solvent is appropriately selected from solvents capable of applying to the stretchable conductive paste.

In the present invention, when a precursor of a material for forming the insulating layer is a liquid, a layer is formed by using the precursor, an appropriate reaction is carried out, and the underlayer can be formed. This is applied to the case where a violet ray curing resin and the like are used.

In addition, when a material for the insulating layer of the present invention is supplied by a film or a sheet prepared from a melt extrusion or a press molding in place of a liquid or a slurry, a processed material in a given shape can be bonded to the substrate using adhesives.

The insulating layer has a thickness of preferably 5 to 300 µm, and more preferably 10 to 150 µm. When the thickness of the insulating layer does not satisfy the range, the durability to be required cannot be obtained in some cases. Also, when the thickness of the insulating layer is beyond the range, steps between the insulating layer part and the non-insulating layer part become large, and there is the possibility that the horse is injured by the scratch.

The stretchable conductive layer constituting the electrode may be exposed and the electrode may be covered with the surface layer of the electrode of which a material has the conductivity and is different from the electrode.

In the present invention, the surface layer of the electrode is a layer in which the surface of the electrode is coated with a material different from the electric wiring. The surface layer of the electrode includes noble metal plating such as gold, platinum, rhodium, solder plating, tin plating and the like.

The surface layer of the electrode of the present invention preferably has the stretchable property of which 10% or more of the stretch can be repeated. In addition, the surface layer of the electrode of the present invention preferably has a fracture elongation of 50% or more. Further, the surface layer of the electrode of the present invention preferably has a tensile modulus of 10 to 500 MPa. In the case where the stretch property is required in the electrode, the surface layer of the electrode can be formed using a carbon paste having the stretchable property.

In the present invention, the carbon paste may be limited to a conductive carbon in the conductive particle used in the stretchable conductive paste for forming the conductive layer. It is preferable that the conductive particle is decreased in an amount of ½ to ⅛ of the metal powder content because the specific gravity of the carbon particle is smaller than that of metal and the carbon particle have a large specific surface area. Other conditions and dispersing methods for obtaining the carbon paste are the same as in the stretchable conductive paste.

The surface layer of the electrode has a thickness of for example 0.5 to 120 µm, preferably 3 to 80 µm, and more preferably 8 to 50 µm.

When the surface layer of the electrode does not satisfy the above thickness, the function for protecting the surface of the electrode is impaired and the durability to be required is not obtained in same cases. In addition, when the surface layer of the electrode is beyond the above thickness, the horse is likely injured with scratch due to the thickness of the electrode part and large steps between parts with the surface layer of the electrode and parts without the surface layer of the electrode.

The belt cover of the present invention can be prepared as follows.

A stretchable conductor sheet is cut such that an external form slightly becomes small (for example by 5 mm) relative to an external form of a first insulating layer, a cut stretchable conductor sheet is laminated on the center of the first insulating layer (for example hot melt urethane sheet) having a given pattern and thickness, a second insulating layer and a cover coating layer (for example polyurethane sheet) having a given pattern and thickness is further laminated on the first insulating layer such that the electrode and the connector connecting part of the stretchable conductive sheet are exposed. Then, a belt cover is thermally bonded to the hot melt urethane sheet of the first insulating layer, and a snap hook is attached to the connector connecting part.

<Constitution of Whole System>

The present invention relates to a belt cover having the electrode for obtaining the bioelectric signal, the electric wiring, and a part for attaching the processing device to terminals of the electric wiring. One example of the constitution of the system for managing the bioelectric signal is explained. The system can include the electrode, the electric wiring, terminals for connection, a processor for processing signals, a primary memory device, a secondary memory device, a GPS receiver, an antenna, a power supply, an outside interface, and the like. The processing device contains those housing same or all of these in the present invention.

In the present invention, an integrated GPS system having a GPS antenna is incorporated in the processing device, and complicated electric wirings such as the electric wirings for GPS antenna to be attached to the body of the horse may not be disposed. As mentioned above, the processing device is disposed at a distance of 1 can to 25 can from the center of the girth, GPS signals can be received without disturbing by the body of the horse, so that the belt cover and the GPS system can be integrated. On the other hand, the GPS processor and the antenna always are not integrated to the processing device, and the GPS processor and the antenna may be disposed on another positions like saddle.

<Combination of Other Bioelectric Information Sensor and Environment Sensor>

In the present invention, sensors capable of measuring a body temperature, a blood pressure, a breathing rate, a blood speed, and a blood gas concentration in addition to the heart rate and the electrocardiogram waveforms are attached to the belt cover and other harnesses, and these can be measured at the same time. In addition, sensors capable of measuring environment conditions such as weather conditions such as outside temperature and moisture can be used in the combination. By these, trainings of the horse can be analyzed in detail.

This application claims the benefit of priorities based on Japanese Patent Application No. 2016-129231, filed on Jun. 29, 2016 and Japanese Patent Application No. 2016-141730, filed on Jul. 19, 2016. The entire content of the specifications of Japanese Patent Application No. 2016-129231, filed on Jun. 29, 2016 and Japanese Patent Application No. 2016-141730, filed on Jul. 19, 2016, is incorporated into this application by reference.

EXAMPLES

The present disclosure will be more specifically described below with reference to Examples, but the present disclosure is not limited to the following Examples, and can be implemented with appropriate modifications within the scope conforming to the purport of what is mentioned above and below herein. All of such modifications are included in the technical scope of the present disclosure.

Production Example

<Preparation of Belt Cover>

A knitting having a tensile deformation of 24% in a bias direction was subjected to a given cutting and sewing to prepare a belt cover shown in FIG. 3 and FIG. 4.

<Polymerization of Synthetic Rubber>

To a stainless reactor equipped with a stirrer and a water-cooled jacket,

| | |
|---|---|
| butadiene | 54 parts by mass |
| acrylonitrile | 46 parts by mass |
| deionized water | 270 parts by mass |
| sodium dodecylbenzene sulfonate | 0.5 parts by mass |
| sodium naphthalene sulfonate condensate | 2.5 parts by mass |
| t-dodecylmercaptan | 0.3 parts by mass |
| triethanol amine | 0.2 parts by mass and |
| sodium carbonate | 0.1 parts by mass | were charged, a bath temperature was kept at 15° C. with the flow of nitrogen, and a mixture was stirred quietly. Then, a aqueous solution of which 0.3 parts by mass of potassium persulfate was dissolved in the 19.7 parts by mass of the deionized water was dropped over 30 minutes, the reaction was continued for 20 hours, and an aqueous solution of which 0.5 parts by mass of hydroquinone was dissolved in 19.5 parts by mass of the deionized water was added thereto to stop the polymerization.

Then, the inside of the reaction container was subjected to reduced pressure, the steam was introduced within the reaction container, and the remaining monomer was collected to distill an unreacted monomer. As a result, a synthetic rubber latex (L1) composed of NBR was obtained.

Sodium chloride and dilute sulfuric acid were added to the resultant synthetic rubber latex (L1), the synthetic rubber latex was aggregated, aggregated synthetic rubber was filtered, deionized water in an amount of 20 times-volume relative to a resin was added by dividing in five times, the resin was re-dispersed and filtered in the deionized water to wash the resin, and the resin was dried in the air to obtain the synthetic rubber resin R1.

The resultant synthetic rubber resin R1 had acrylonitrile content of 43% by mass, Mooney viscosity of 53, and tensile modulus of 31 MPa.

[Preparation of Stretchable Conductive Paste]

The synthetic rubber resin (R1) as the stretchable resin obtained in the above in an amount of 12 parts by mass, and isophorone in an amount of 30 parts by mass were mixed and stirred to obtain a binder resin composition A1. Then, 58.0 parts by mass of aggregated silver powder like amorphous (G-35, manufactured by DCWA Electronics, Inc. an average particle diameter of 5.9 μm) as silver powder like amorphous was added to the binder resin composition Al to uniformly mix these, and the mixture was dispersed by three roll mil to obtain a stretchable conductive paste C1.

The resultant stretchable conductive paste C1 was coated on a release sheet using a barcoater, and these were dried for 30 minutes or more in a hot-air dryer oven at 120° C. If necessary, the same operation was repeated such that the thickness of the stretchable conductive layer was 70 nm, a stretchable conductive layer (stretchable conductive sheet) having a release sheet was prepared, and the sheet contained an electrode (area contacting with the body of the horse of 60 cm$^2$), an electric wiring and a connector, and electrical contacts (snap hooks) of the connector were disposed at distances of 2.5 cm and 7.5 cm from the center of the longitudinal direction of the belt cover to the left sides, respectively.

The stretchable conductor sheet was cut such that an external form slightly become small (for example by 5 mm) relative to an external form of a first insulating layer, a cut stretchable conductor sheet was laminated on the center of the first insulating layer (for example hot melt urethane sheet) having a given pattern and thickness of 50 μm, a second insulating layer and a cover coating layer (for example polyurethane sheet) having a given pattern and a thickness of 50 μm was laminated on the first insulating layer such that the electrode and the connector connecting part of the stretchable conductive sheet were exposed. Then, a belt cover was thermally bonded to the hot melt urethane sheet of the first insulating layer, and snap hooks were attached to the connector connecting part (see FIG. 3).

Example 1

The obtained belt cover having a thickness of 1.4 mm and a length of 95 can was used as a girth cover.

Concretely, a processing device was attached to the belt cover, the belt cover was attached to the girth for attaching the saddle for riding to the body of the horse to prepare a harness, and the resultant harness was worn to a thoroughbred horse (three-year-old male). A heart rate monitor manufactured by Polar was used as the processing device. Also, a GPS system was used to measure a speed at a speed accuracy of 0.36 km/h. The measurement was carried out in a 1000 m dirt course at a farm of Japan Hokkaido Urakawa-gun and a heart rate data was measured over a still state, a trot, and a top speed at a state that the human rides on the horse. Measured results are shown in FIG. 5.

Example 2

The belt cover prepared in the above preparation example was attached to the belt for the horse having a length of 180 cm. The belt and the belt cover were attached to the girth of the thoroughbred horse (three-year-old male) such that the electrodes were disposed at a left side and a right side relative to the center of the belly. The horse was put on a treadmill for the horse at a state that the horse does not carry a human, walking and speeds were changed in the orders of a walk, a trot, a rising trot, a cantor, and a gallop, to measure the heart rate data. The heart rate monitor manufactured by Polar was used as the processing device. As a result, electrocardiogram waveforms could be measured in all stages of walking and speeds.

Example 3

The belt cover prepared in the above preparation example was attached to the specialized saddle of Hanover species (ten-year-old gelding). Remote electrocardiogram waveforms were measured using the heart rate monitor manufactured by Polar in jumping equestrian events. From the start to the end of the competition, the electrocardiogram waveforms were measured without troubles.

INDUSTRIAL APPLICABILITY

As mentioned above, the electrocardiogram waveforms of the horse at remote definitely can be measured over the whole behavior patterns by applying the present invention. Many data such as physical conditions, fatigue degrees can be read from electrocardiogram data. The horse can be definitely managed based on the data in polo in which the horse is exchanged according to fatigue degree of the horse, in addition to competition, supporting training, equestrian event as exemplified in Examples.

DESCRIPTION OF THE REFERENCE NUMERICAL

1: body of horse
2: saddle
3: belt
4: jockey
5: belt cover
6: electrode for contacting with surface of body of horse
7: electric wiring
8: cover for connector and device
9: snap button (connector)
10: hook and loop fastener
11: connector connecting part
12: hook and loop fastener

The invention claimed is:

1. A belt cover for attaching to a horse, comprising at least the following (1) to (3):
(1) an electrode for detecting a bioelectric signal by contacting with the surface of a body of the horse,
(2) an electric wiring, and
(3) a connector for connecting with the electric wiring through a part for connecting with the connector and the electric wiring,
wherein each of the electrode and the electric wiring comprises a stretchable conductor comprising a conductive particle comprising a silver particle and a binder resin,
the stretchable conductor of the electrode and the electric wiring has a sheet resistance of $0.1\Omega_\square$ or less,
an insulating layer is laminated on the electric wiring, and the electrode and the electric wiring are integrally formed without joints which prevents the electric wiring from being disconnected during physical activities of the horse and also prevents water or sweat from the horse from entering between the electrode and the electric wiring which makes it possible to continue to trace the physical activities of the horse at times of rainfall and also at times of the physical activities being intense, resulting in the sweat from the horse,
wherein the electrode, the electric wiring, and the part for connecting with the connector and the electric wiring are formed from a stretchable conductor sheet composed of the stretchable conductor,
wherein the stretchable conductive sheet constituting the electrode, the electric wiring, and the part for connecting with the connector and the electric wiring has a thickness of from 0.02 mm to 2.0 mm, and
wherein the connector is connected with at least one device selected from any one of the following b) to d):
b) a device for memorizing the bioelectric signal to be detected,
c) a wireless communication device for transmitting the bioelectric signal outside, and
d) a device for providing a power.

2. The belt cover according to claim 1, wherein the binder resin comprises a thermoplastic resin, a thermosetting resin, or a rubber, which has a tensile modulus of 1 to 1000 MPa.

3. The belt cover according to claim 2, wherein the binder resin comprises the rubber.

4. The belt cover according to claim 1, wherein the bioelectric signal comprises electrocardiographic waveforms comprising at least heart rate.

5. The belt cover according to claim 1, wherein the electrode is disposed at a distance of 10 cm to 45 cm from the center of a longitudinal direction of the belt cover to the right and left sides, respectively.

6. The belt cover according to claim 1, wherein the connector is disposed at a distance of 1 cm to 25 cm from the center of a longitudinal direction of the belt cover to the right and left sides, respectively.

7. The belt cover according to claim 1, wherein the connector is covered with a cover for the connector and the device so as not to contact with the belly of the horse when the belt cover is attached to the horse.

8. The belt cover according to claim 1, wherein one electrode has an area of from 20 cm$^2$ to 150 cm$^2$ when contacting with the surface of the body of the horse.

9. The belt cover according to claim 1, wherein a substrate constituting the belt cover comprises a laminate having two or more clothes and an unfixed part is formed between two or more clothes, and the laminate surrounds a belt when the belt cover is attached to the belt.

10. The belt cover according to claim 1, wherein the belt cover is folded relative to a central axis of a width direction of the belt cover, such that the electrode contacts with the surface of the body of the horse, and the connector and the cover for the connector and the device are disposed on the opposite side to the surface of the body of the horse.

11. A girth cover for attaching a saddle for riding to a horse, comprising at least the following (1) to (3):
   (1) an electrode for detecting a bioelectric signal by contacting with the surface of a body of the horse,
   (2) an electric wiring, and
   (3) a connector for connecting with the electric wiring through a part for connecting with the connector and the electric wiring,
   wherein each of the electrode and the electric wiring comprises a stretchable conductor comprising a conductive particle comprising a silver particle and a binder resin,
   the stretchable conductor of the electrode and the electric wiring has a sheet resistance of $0.1\Omega_\square$ or less,
   an insulating layer is laminated on the electric wiring, and
   the electrode and the electric wiring are integrally formed without joints which prevents the electric wiring from being disconnected during physical activities of the horse and also prevents water or sweat from the horse from entering between the electrode and the electric wiring which makes it possible to continue to trace the physical activities of the horse at times of rainfall and also at times of the physical activities being intense, resulting in the sweat from the horse,
   wherein the electrode, the electric wiring, and the part for connecting with the connector and the electric wiring are formed from a stretchable conductor sheet composed of the stretchable conductor,
   wherein the stretchable conductor sheet constituting the electrode, the electric wiring, and the part for connecting with the connector and the electric wiring has a thickness of from 0.02 mm to 2.0 mm, and
   wherein the connector is connected with at least one device selected from any one of the following b) to d):
   b) a device for memorizing the bioelectric signal to be detected,
   c) a wireless communication device for transmitting the bioelectric signal outside, and
   d) a device for providing a power.

12. The girth cover according to claim 11, wherein the binder resin comprises a thermoplastic resin, a thermosetting resin, or a rubber, which has a tensile modulus of 1 to 1000 MPa.

* * * * *